United States Patent [19]

Cleaveland

[11] 4,026,591
[45] May 31, 1977

[54] CONTACT LENS HANDLING TOOLS
[76] Inventor: John A. Cleaveland, Rte. 1, Box 61, Portland, Oreg. 97231
[22] Filed: Mar. 15, 1976
[21] Appl. No.: 667,268
[52] U.S. Cl. .............................. 294/1 CA; 294/64 R
[51] Int. Cl.² .......................................... A61F 9/00
[58] Field of Search ........ 294/1 R, 1 CA, 20, 64 R; 128/233, 249, 303 R; 206/5.1; 351/160

[56] References Cited
UNITED STATES PATENTS

| | | | |
|---|---|---|---|
| 2,637,587 | 5/1953 | Robinson | 294/20 |
| 2,919,696 | 1/1960 | Rinaldy | 294/1 CA UX |
| 3,091,328 | 5/1963 | Leonardos | 294/1 CA UX |
| 3,424,486 | 1/1969 | Corley | 294/64 R |
| 3,600,028 | 8/1971 | Henning | 294/1 CA |
| 3,645,576 | 2/1972 | Horres | 294/1 CA |
| 3,910,618 | 10/1975 | Massenz | 294/1 CA |

*Primary Examiner*—Johnny D. Cherry
*Attorney, Agent, or Firm*—Klarquist, Sparkman, Campbell, Leigh, Hall & Whinston

[57] ABSTRACT

A light passing, contact lens inserting tube having an annular lens holder is inserted through a plunger tube in an extended position and into a friction collar freely slidable in a tubular handle mounted fixedly on the plunger tube which is spring urged to a retracted position relative to an eye cup. Then a contact lens is lightly adhered to the holder by wetting fluid, the plunger tube is released to move the lens back into the eye cup, with the tool extending upwardly, and the plunger tube is extended from its retracted position to allow the inserting tube and lens to move by gravity toward the eye to place the lens very gently on the eye. A steady rest on the eye cup engages the cheek to insure that the tool is perpendicular to the eye. The lens inserting tube may be removed and replaced with a lens removing tube with a suction cup flexibly mounted thereon to remove the contact lens from the eye.

In an alternate lens handling tool, a plunger tube is spring urged to a retracted position relative to an eye cup and an annular lens holder is carried by a tubular carrier freely slidable in a cap fitting on one end of the plunger tube. Another alternate lens handling tool has a carrier tube slidable relative to an eye cup and carries an annular lens holder by a tubular bellows.

15 Claims, 6 Drawing Figures

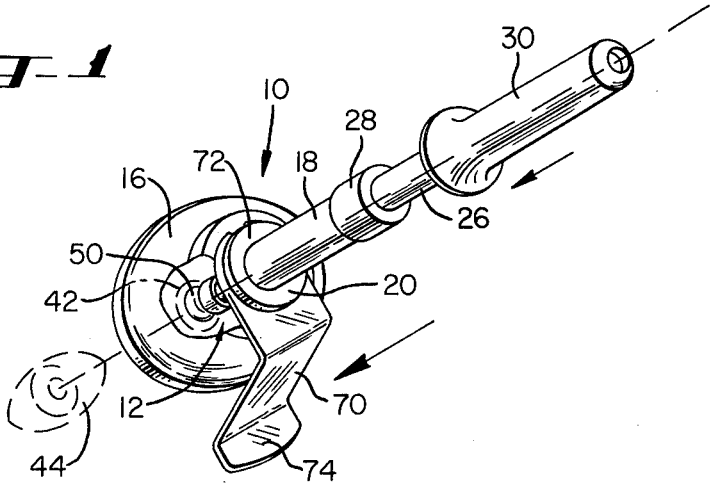
Fig. 1
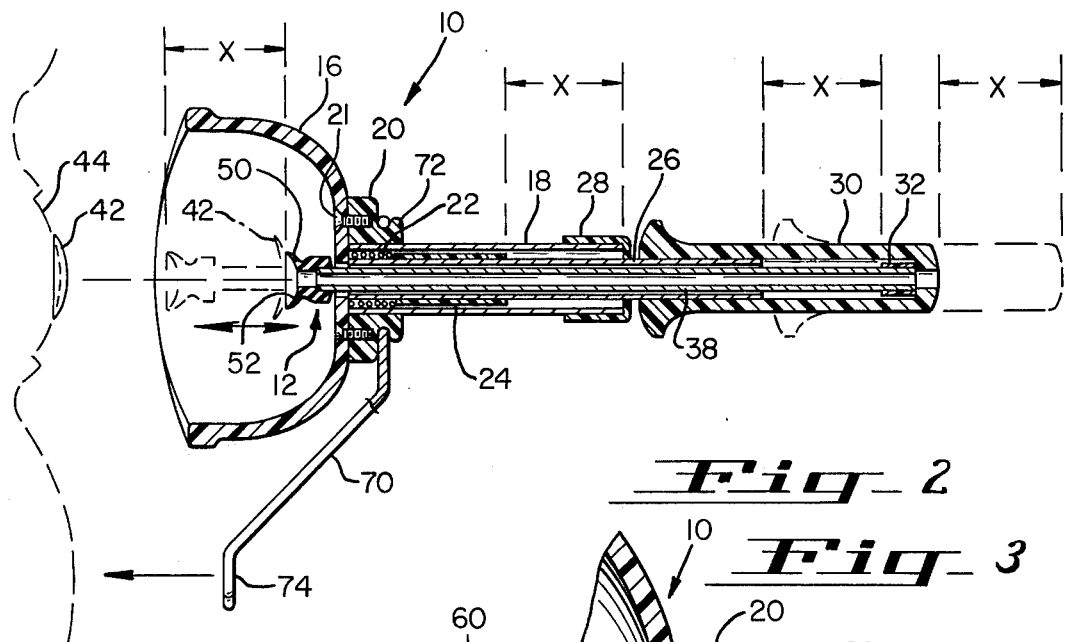
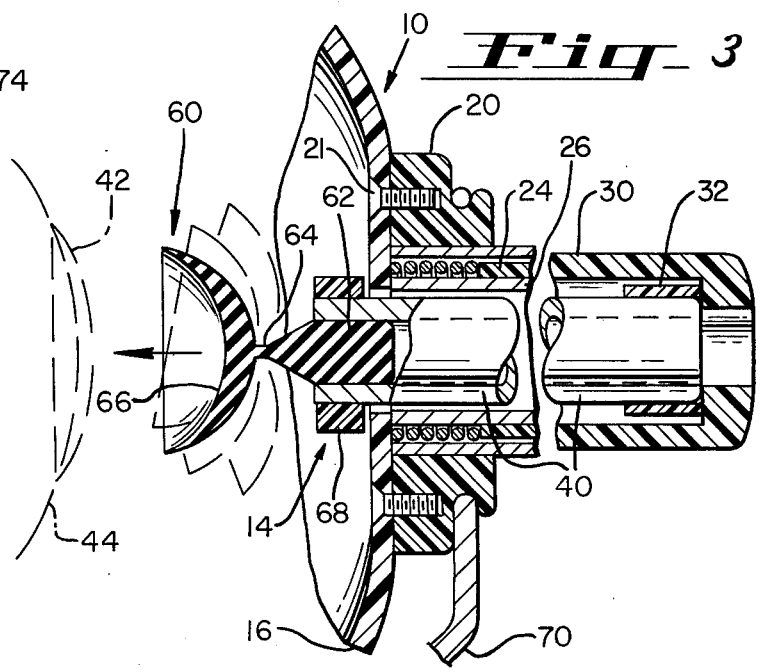
Fig. 2
Fig. 3

CONTACT LENS HANDLING TOOLS

DESCRIPTION

This invention relates to an improved contact lens handling tool, and has for an object thereof the provision of an improved contact lens handling tool.

Another object of the invention is to provide a contact lens handling tool which has a free floating lens holder.

A further object of the invention is to provide a contact lens handling tool which has a free floating lens holding suction cup which is flexibly supported to permit the cup to align itself perpendicularly to the lens.

Another object of the invention is to provide a contact lens handling tool which is easily positioned perpendicular to the eye.

Another object of the invention is to provide a lens handling tool including a carrier tube slidable in a cap fitting on one end of a spring retracted carrier tube and carrying an annular lens holder.

Another object of the invention is to provide a lens handling tool including a tubular bellows carrying a lens holder and carried by a carrier tube.

In the drawings:

FIG. 1 is a perspective view of an improved contact lens handling tool forming one embodiment of the invention;

FIG. 2 is an enlarged, longitudinal sectional view of the tool of FIG. 1;

FIG. 3 is a view like FIG. 2 but with a lens remover substituted for a lens holder shown in FIG. 2;

Figure 4:
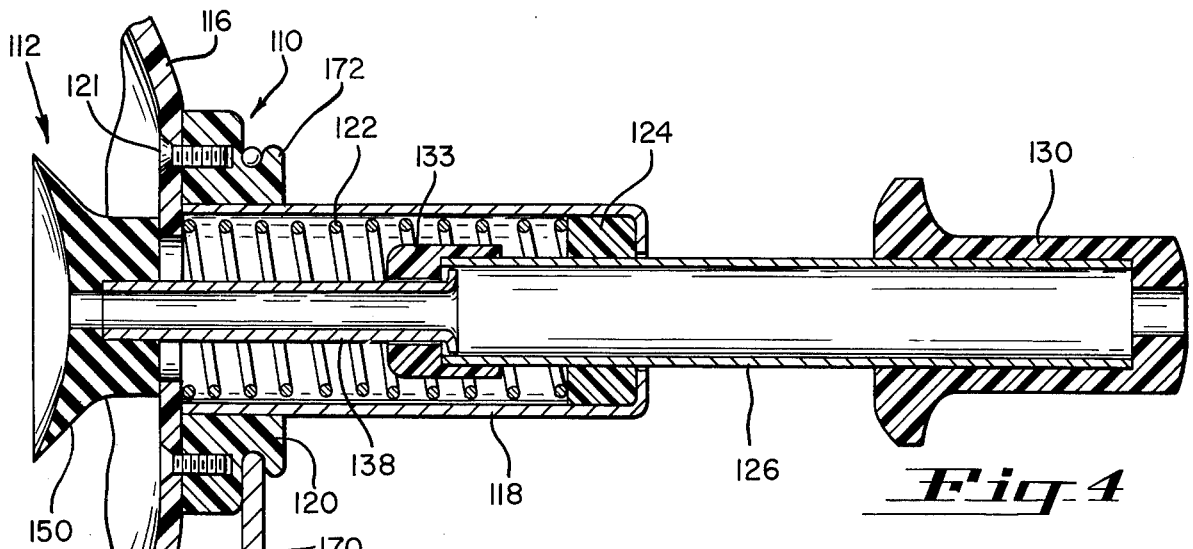
FIGS. 4 and 5 are longitudinal sectional views of an improved contact lens handling tool forming an alternate embodiment of the invention; and, FIG. 6 is a longitudinal sectional view of an improved contact lens handling tool forming an alternate embodiment of the invention.

Referring now in detail to the drawings, there is shown therein an improved contact lens handling tool forming one embodiment of the invention and including a freely manipulatable actuator or positioner 10 adapted to have inserted thereinto and hold selectively in a free floating manner either a lens inserter 12 or lens remover 14. The actuator includes an eye cup 16 adapted to bottom in the outer peripheral portion of the eye socket of the user.

A stainless steel outer tube 18 extends into and is cemented in a socket portion 20 secured by screws 21 to the cup 16, and a soft action, stainless steel spring 22 seats against the bottom of the socket and against an elastomer collar 24 fixed to a stainless steel plunger tube 26. The collar 24 normally abuts an elastomer cap 28 fitting tightly on the outer tube 18. The socket portion 20 may be integral with the cup. A tubular handle 30, which may be of a tough plastic material, is fixed as by an adhesive to one end portion of the plunger tube 26 and is counterbored.

A friction collar or retaining sleeve 32 fits loosely and slidably in the handle 30. The collar may be of brass or other ductile, non-corrosive metal, or of a suitable plastic. The collar fits sufficiently tightly on a stainless steel tube 38 of the lens inserter 12 and a stainless steel tube 40 of the lens remover 14 to hold the weight of the inserter (or remover) and a contact lens 42 for eye 44 of the user. The tubes 38 and 40 are quite light in weight, and the interior surface of the tube 38 is highly polished to provide a good light path therethrough. Each of the tubes 38 and 40 is easily pulled out of and inserted into the collar 32, which is trapped in the counterbore in the handle 30 against removal. The inserter 12 includes an annular cup-like holder 50 cemented or otherwise fixed to one end of the tube 38, and the holder 50 when dished face 52 thereof is wetted with contact lens wetting solution adheres to the contact lens 42 sufficiently to hold the lens for placement on the eye 44.

The lens remover 14 includes a rubber or rubber-like suction cup 60 having a shank 62 cemented to the interior of one end portion of the tube 40. A reduced or necked down portion 64 of the shank is very flexible to permit tilting of cup portion 66 to enable the cup portion to become perpendicular to the lens and adhere thereto, when the cup portion is covered with lens wetting solution, and the cup portion is brought into engagement with the lens. The reduced portion 64 is, in effect, a universal joint permitting limited tilting of the cup portion. This feature also aids in painless, comfortable removal of the lens by allowing some eye movement without causing the lens to slide on the eyeball.

A stop collar 68 is fixed to the end portion of the tube 40 to limit travel of the tube 40 into the tubes 18 and 26 and the handle 30. This prevents the remover 14 from falling further into the eye cup and tubes.

A strap-like steady rest or brace 70 is secured to boss portion 72 of the cup 16. The brace preferably is of aluminum or other ductile material and can be bent initially to position a foot 74 so that the inserter 12 (or the remover 14) is perpendicular to the central portion of the eye 44 when the foot is on the cheek of the user and the cup 16 is seated in the eye socket.

OPERATION

First the lens inserter (or remover) must be put into the actuator. This is done by depressing the handling 30 fully until it seats on cap 28. Then the tube 38 is inserted through eye cup 16 and tube 26 to engage with collar 32, the holder 50 then being at or near the bottom of the cup 16 as shown in FIG. 2. Then, the handle 30 is released, and the spring 22 moves the plunger tube 26 and the handle to their normal or retracted positions. This holds the holder 50 retracted to the bottom of the cup. The user then wets the holder 50 and places the lens 42 thereon, and then places the cup 16 against the eye socket and the foot 74 against the cheek of the user. The cup 16 holds the eyelids back and supports the actuator. Then, with the head of the user tilted back, he looks through polished tube 38 and the tubular handle 30 to precisely center the lens and then pushes the handle 30 down to let the inserter 12 lower the lens gently into centered contact with the eye 44. Then, the handle is released and the inserter is gently pulled away from the lens. Note that the handle does not push the inserter but can only pull it. The inserter is advanced toward the eye only be gravity as the handle is depressed. This means the operator cannot push the inserter through his eye by depressing the handle too far or too hard.

To remove the contact lens 42 from the eye 44, the inserter 12 is pulled out of the actuator and with the handle 30 depressed against the cap 28, the tube 40 is inserted into the actuator until the tube 40 slides into the collar 32 and is frictionally gripped thereby, the stop collar 68 being near or in contact with the bottom of the cup 16. The user wets the cup 66 with the wetting solution. Then, the user places the cup 16 against the periphery of the eye socket and the foot 72 against the cheek. Then, with the head tilted back, the plunger 26 is fully depressed and gravity moves the remover 14 and the cup 60 downwardly until the cup gently engages and grips the lens 42 on the eye 44. The handle 30 is then released and the plunger tube 26 and the remover 14 are retracted to gently pull the contact lens away from the eye 44.

A comparatively low degree of skill is needed to use the above-described tool. The eye cup 16 serves to hold the eyelids back and, at the same time, provides for support and positioning of the device. The steady rest 70 enables the eye cup plunger to be readily positioned at right angles to the eye. Additional alignment is provided by the beam of light (the source being any overhead light) which enters a light aperture at the far end of the plunger and passes through a hole in the holder 50 and through the contact lens which has been placed on the holder, and if desired, a collecting and collimating lens could be mounted in the aperture in the handle. The hole serves the dual function of admitting light and providing an absence of suction to the contact lens so that release will occur when the lens meets the eye. By tipping the tool "to and fro" slightly, the user determines the best alignment by seeking that position which offers the brightest light beam. At the same time, the eyeball is correctly positioned due to the gaze being fixed on the light, thus insuring that the contact will be placed centrally on the eye. At this point, the user's head is tipped back sharply. To insert the contact, he simply depresses the plunger fully and then releases it. The procedure for removal is the same except that the remover 14 is provided which has no hole for light to pass through and consequently exerts a strong suction when it touches the lens. The reduced cross section 64 at its neck allows it to flex or tip to align itself so that good connection is made with the contact lens. Thus, insertion or removal of the contact lens is completely free of any necesssity for manual dexterity, steady-handedness, or light touch.

The insertion and removal are gentle. At no time is the eye poked, grazed or irritated. This is accomplished by the free floating nature of the tube 38 (or 40). When the plunger handle 30 is depressed, the tube 38 within it is lowered to move the contact lens toward the eye. At this point, the tube 38 is free to cease its travel, and is urged toward the eye only by means of gravity, even though the plunger 26 continues forward to the end of its stroke. In this way, insertion (or removal) is more delicate and correct than is normally possible with the human finger.

The tool is safe. It is checked for proper operation each time before use simply by inverting the device, depressing the plunger, and observing that no motion of the inserter or remover occurs. Thus, any possibility of injury or irritation to the eye caused by jabbing is eliminated. Both cups 50 and 60 are permanently attached to their tubes so that there is no chance of a naked tube end touching the eye. The inserter and remover are easily exchanged by depressing the plunger handle, pulling out the one in place, and pushing in the other.

The tool 10 also saves time and patience since success is usually achieved with the first try. The risk of lens loss accompanied with fingertip handling is also greatly reduced, the contact lens being situated within the confines of the eye cup. In short, the tool 10 makes it possible for many individuals to wear contact lenses who would not be able to do so otherwise. For those cataract patients who have experienced any difficulty with contact insertion and removal, the tool employs features which make the process easier, speedier, safer and more comfortable.

While, as described above, the tubes or slide members 38 and 40 are freely slidable, the tool would work well and safely with a very light spring urging the tube 38 (or the tube 40) toward its extended position, the very light spring permitting substantially free floating movement of the tubes 38 and 40.

Figure 5:
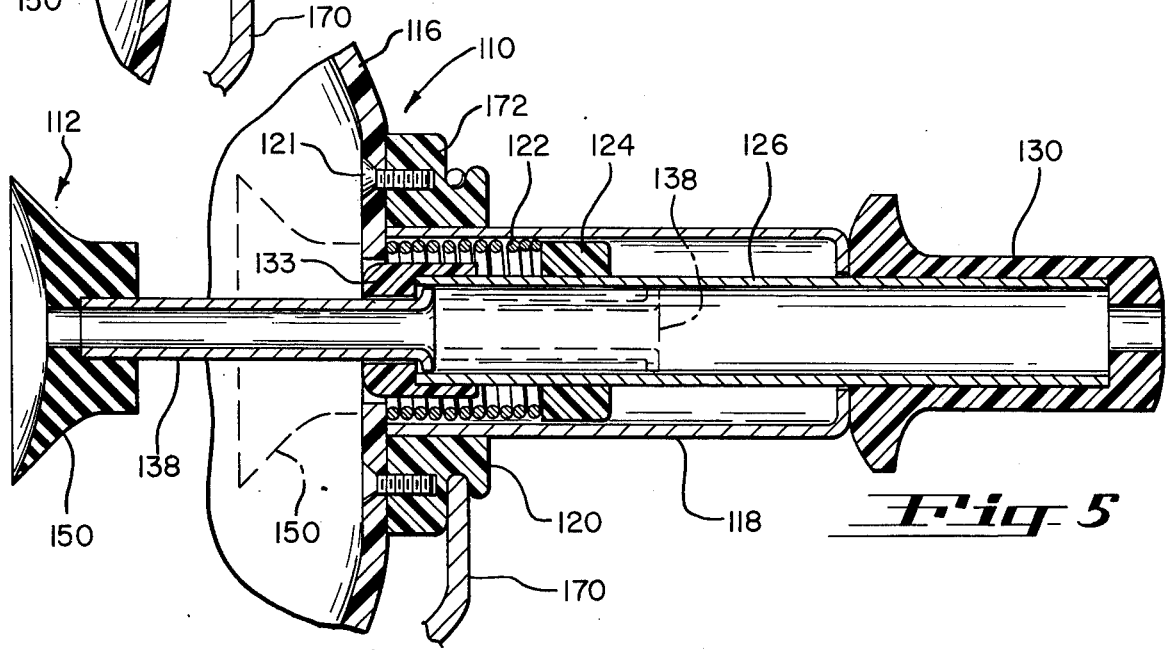
Figure 6:
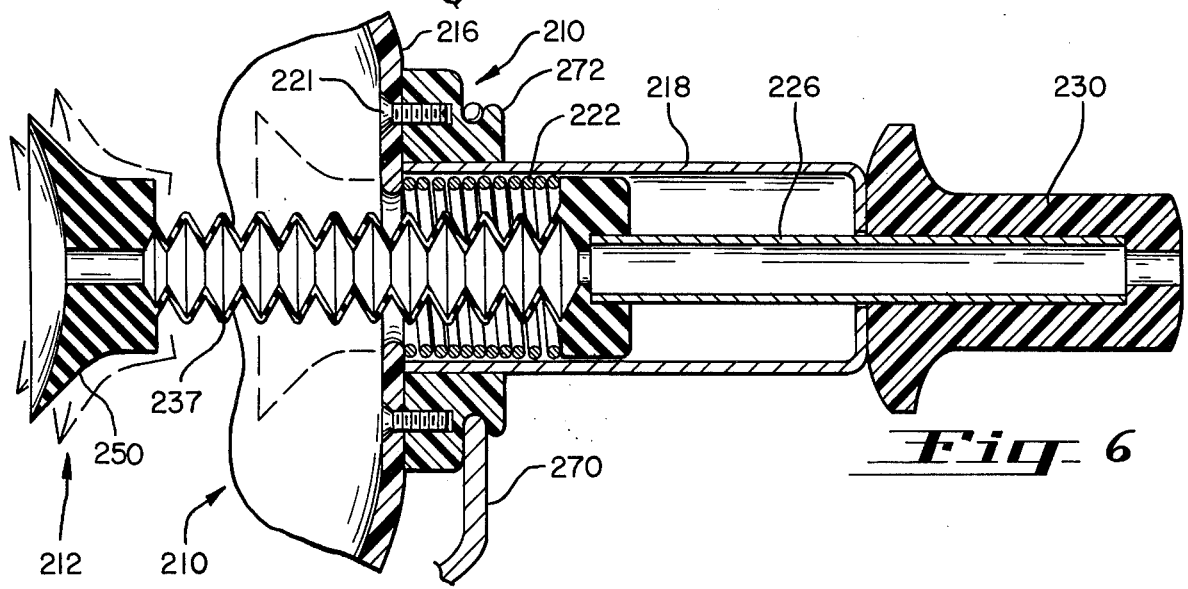

EMBODIMENT OF FIGS. 4 and 5

A contact lens holding tool forming an alternate embodiment of the invention includes an actuator 110 for selectively carrying in a free floating manner a lens inserter 112 or a lens remover (not shown). The actuator includes an eye cup 116 and a handle-like outer tube 118 cemented in a socket portion 120 fastened to the cup 116. A soft action spring 122 urges a plunger tube 126 toward a retracted position through a collar 124 fixed to the tube 126. A tubular handle 130 is fixed to one end of the tube 126 and a cap 133 is removably secured by friction to the other end of the tube 126. A carrier tube 138 is freely slidable in the cap 133 and slidably carries an annular lens holding cup 150. The tube 138 could be a solid, light transmitting plexiglass rod, if desired. The tube 138 is slidable by gravity to lightly position a contact lens on the eye. The remover (not shown) is like the inserter but has a vacuum cup rather than the cup 150. The insertion and removal of the lens is like those described above in connection with the tool of FIGS. 1–3, it being noted that, when the inserter is in the actuator 110, a light passage for alignment of the lens with the eye is provided.

EMBODIMENT OF FIG. 6

A contact lens holding tool forming an alternate embodiment of the invention includes an actuator or positioner 210 including a tubular lens holder 212 freely slidable relative to a guide tube 218 fixed to an eye cup 216. The holder 212 includes an annular cup 250 cemented to a very flexible rubber or plastic tubular bellows 237 secured at its other end to a carrier tube 226 slidable in the tube 218. A tubular handle 230 is fixed to the tube 226. The bellows 237 is easily compressed longitudinally. The holder 212 serves both as an inserter and a remover, a finger being placed over the end of the handle 230 for removal to cause the cup 250 to be a vacuum cup, the bellows preferably being longitudinally compressed somewhat to increase the vacuum. The insertion and removal are otherwise the same as those of the earlier described embodiments. The bellows, as well as giving a soft spring action, acts as a soft universal joint to permit the lens to seat on the eye, and, during removal, the cup 250 to seat on the lens.

The suction cup 60 may be of transparent or translucent material to provide light for alignment of the tool during lens removal. Also, it is contemplated that the bellows 237 can be used by itself, without the cups 216 and 250 and the tube 218 and with or without the handle 230 and tube 226 to provide a soft inserter and remover.

What is claimed is:
1. In an improved contact lens handling tool,
an eye cup, an elongated guide member fixed to and carrying the eye cup, a manually depressable plunger slidably mounted on the guide member, lens holding means, an elongated slide member carrying the lens holding means, and substantially freely slidable relative to the guide member and the plunger, and stop means engageable by the plunger for holding the slide member in a retracted position when the plunger is in its extended position and permitting the slide member to move toward the eye by gravity when the plunger is depressed.

2. The improved contact lens handling tool of claim 1 wherein the guide member and the plunger are tubular and the plunger is telescopically mounted in the guide member, the slide member being slidably mounted in the plunger.

3. The improved contact lens handling tool of claim 1 wherein the stop means is a collar freely movable relative toward and away from one end of the plunger and frictionally holding the slide member.

4. The improved contact lens handling tool of claim 1 wherein the lens holding means is an annular cup and the slide member has a light passage extending therealong.

5. The improved contact lens handling tool of claim 1 wherein the lens holding means is a suction cup.

6. The improved contact lens handling tool of claim 5 including means mounting the suction cup on the slide member for limited universal movement relative thereto.

7. The improved contact lens handling tool of claim 1 wherein different slide members may be inserted, one specialized for lens removal and one for inserting.

8. In an improved contact lens handling tool, a lens holding cup, an elongated slide member holding the cup, an elongated plunger member carrying the slide member for substantially free lost motion movement therebetween, a guide member mounting the plunger member telescopically, eye cup means carried by the guide member, and means urging the plunger member toward a retracted position in which the lens holding cup is retracted into the eye cup.

9. In an improved contact lens handling tool, a lens holding cup, an elongated light transmitting slide member holding the cup, an elongated tubular plunger member carrying the slide member for substantially free lost motion movement therebetween, a guide member mounting the plunger member telescopically, eye cup means carried by the guide member, means urging the plunger member toward a retracted position in which the lens holding cup is retracted into the eye cup, and cap means guiding the slide member and detachably mounted on the plunger member.

10. The improved contact lens handling tool of claim 9 wherein the slide member is tubular.

11. The improved contact lens handling tool of claim 10 wherein the cap means frictionally engages the plunger member to hold the cap means on the plunger member.

12. An improved contact lens handling tool comprising:

an elongated, flexible tubular bellows means having lens-holding means on an end thereof, the bellows means comprising an elastomer tube having a plurality of convolutions and being flexible both laterally and axially so that a lens may be moved gently to the eye, the bellows means having a manually closable opening at the opposite end thereof adapted to be closed by the user.

13. The improved contact lens handling tool of claim 12 wherein the lens holding means is an annular cup.

14. The improved contact lens handling tool of claim 13 including an elongated plunger member carrying the bellows means, a guide member mounting the plunger member telescopically, eye cup means carried by the guide member, and means urging the plunger member toward a retracted position in which the lens-holding means is retracted into the eye cup.

15. The improved contact lens handling tool of claim 14 wherein the plunger member is tubular.

* * * * *